United States Patent [19]
Snodgrass et al.

[11] Patent Number: 5,856,098
[45] Date of Patent: Jan. 5, 1999

[54] DETECTION OF A LEPTIN RECEPTOR VARIANT

[75] Inventors: H. Ralph Snodgrass, Powell; Joseph Cioffi, New Albany; Thomas Joel Zupancic, Worthington; Alan Wayne Shafer, Lancaster, all of Ohio

[73] Assignee: Progenitor, Inc., Menlo Park, Calif.

[21] Appl. No.: 588,190

[22] Filed: Jan. 18, 1996

Related U.S. Application Data

[63] Continuation-in-part of Ser. No. 355,888, Dec. 14, 1994, which is a continuation-in-part of Ser. No. 306,231, Sep. 14, 1994.

[51] Int. Cl.$^6$ .................................................. C12Q 1/68
[52] U.S. Cl. ........................ 435/6; 435/7.1; 435/7.2; 536/23.5
[58] Field of Search ................................. 435/6, 7.1, 7.2, 435/172.3; 536/23.5

[56] References Cited

FOREIGN PATENT DOCUMENTS

| | | |
|---|---|---|
| 0 409 607 A2 | 1/1991 | European Pat. Off. . |
| 0 521 156 A1 | 1/1993 | European Pat. Off. . |
| WO 88/02757 | 4/1988 | WIPO . |
| WO 93/10151 | 5/1993 | WIPO . |

OTHER PUBLICATIONS

Tartaglia et al., "Identification and Expression Cloning of a Leptin Receptor, OB–R", Cell 83:1263–1271, Dec. 29, 1995.
Scott, J., "New chapter for the fat controller", Nature 379:113–114, Jan. 11, 1996.
Barinaga, M., "Obesity: Leptin Receptor Weighs In", Science 271:29, Jan. 5, 1996.
Pelleymounter et al., 1995, "Effects of the obese Gene Product on Body Weight Regulation in ob/ob Mice," Science 269:540–549.
Beckmann et al., 1994, "Molecular characterization of a family of ligands for eph–related tyrosine kinase receptors," The EMBO Journal 13(16):3757–3762.
Miyajima et al., 1993, "Receptors for Granulocyte–Macrophage Colony–Stimulating Factor, Interleukin–3, and Interleukin–5," Blood 82(7):1960–1974.
Saito et al., 1992, "Molecular Cloning of a Murine Il–6 Receptor–Associated Signal Transducer, gp 130, and its Regulated Expression in Vivo," J. Immunol. 148(12):4066–4071.
Park et al., 1992, "Cloning of the low–affinity murine granulocyte–macrophage colony–stimulating factor receptor and reconstitution of a high–affinity receptor complex," Proc. Natl. Acad. Sci. U.S.A. 89:4295–4299.
Miyajima et al., 1992, "Cytokine Receptors and Signal Transduction," Ann. Rev. Immunol. 10:295–331.

Truett et al., 1991, "Rat obesity gene fatty (fa) maps to chromosome 5: Evidence for homology with the mouse gene diabetes (db)," Proc. Natl. Acad. Sci. U.S.A. 88:7806–7809.
Larsen et al., 1990, "Expression Cloning of a Human Granulocyte Colony–stimulating Factor Receptor: A Structural Mosaic of Hematopoietin Receptor, Immunoglobulin, and Fibronectin Domains," J. Exp. Med. 172:1559–1570.
Hibi et al., 1990, "Molecular Cloning and Expression of a Il–6 Signal Transducer, gp130," Cell 63:1149–1157.
Hayashida et al., 1990, "Molecular cloning of a second subunit of the receptor for human granulocyte–macrophage colony–stimulating factor (GM–CSF): Reconstitution of a high–affinity GM–CSF receptor," Proc. Natl. Acad. Sci. U.S.A. 87:9655–9659.
Harada et al., 1990, "Expression Cloning of a cDNA Encoding the Murine Interleukin 4 Receptor Based on Ligand Binding," Proc. Natl. Acad. Sci. U.S.A. 87:857–861.
Gorman et al., 1990, "Cloning and Expression of a Gene Encoding an Interleukin 3 receptor–Like Protein: Identification of Another Member of the Cytokine Receptor Gene Family," Proc. Natl. Acad. Sci. U.S.A. 87:5459–5463.
Fukunaga et al., 1990, "Expression Cloning of a Receptor for Murine Granulocyte Colony–Stimulating Factor," Cell 61:341–350.
Cosman et al., 1990, "A new Cytokine Receptor Superfamily," TIBS 15:265–269.
Bazan, 1990, "Structural Design and Molecular Evolution of a Cytokine Receptor Superfamily," Proc. Natl. Acad. Sci. U.S.A. 87:6934–6938.
Bahary et al., 1990, "Molecular Mapping of the Mouse db Mutation," Proc. Natl. Acad. Sci. U.S.A. 87:8642–8646.
Mosley et al., 1989, "The Murine Interleukin–4 Receptor: Molecular Cloning and Characterization of Secreted and Membrane Bound Forms," Cell 59:335–348.
Gearing et al., 1989, "Expression cloning of a receptor for human granulocyte–macrophage colony–stimulating factor," The EMBO Journal 8(12):3667–3676.
Yamasaki et al., 1988, "Cloning and Expression of the Human Interleukin–6 (BSF–2/IFNβ 2) Receptor," Science 241:825–828.
Gearing et al., 1987, "Molecular Cloning and Expression of cDNA Encoding a Murine Myeloid Leukaemia Inhibitory Factor (LIF)," The EMBO Journal 6:3995–4002.

Primary Examiner—John Ulm
Attorney, Agent, or Firm—Pennie & Edmonds LLP

[57] ABSTRACT

The present invention relates to a variant form of the receptor for the obese gene product. In particular, the invention relates to methods of detecting this receptor variant in cells and tissues of obese individuals. In addition, it relates to methods of inhibiting or down-regulating expression of this variant in cells to augment their responsiveness to weight regulation by leptin as well as methods of using compounds to directly activate signal transduction pathways associated with this ligand-receptor system.

19 Claims, 7 Drawing Sheets

```
              9              18              27              36              45              54
GCG CGC GCG ACG CAG GTG CCC GAG CCC CGG CCC GCG CCC ATC TCT GCC TTC GGT
--- --- --- --- --- --- --- --- --- --- --- --- --- --- --- --- --- ---
 A   R   A   T   Q   V   P   E   P   R   P   A   P   I   S   A   F   G 63              72              81              90              99             108
CGA GTT GGA CCC CCG GAT CAA GGT GTA CTT CTC TGA AGT AAG ATG ATT TGT CAA
--- --- --- --- --- --- --- --- --- --- --- --- --- --- --- --- --- ---
 R   V   G   P   P   D   Q   G   V   L   L   *   S   K   M   I   C   Q 117             126             135             144             153             162
AAA TTC TGT GTG GTT TTG TTA CAT TGG GAA TTT ATT TAT GTG ATA ACT GCG TTT
--- --- --- --- --- --- --- --- --- --- --- --- --- --- --- --- --- ---
 K   F   C   V   V   L   L   H   W   E   F   I   Y   V   I   T   A   F 171             180             189             198             207             216
AAC TTG TCA TAT CCA ATT ACT CCT TGG AGA TTT AAG TTG TCT TGC ATG CCA CCA
--- --- --- --- --- --- --- --- --- --- --- --- --- --- --- --- --- ---
 N   L   S   Y   P   I   T   P   W   R   F   K   L   S   C   M   P   P 225             234             243             252             261             270
AAT TCA ACC TAT GAC TAC TTC CTT TTG CCT GCT GGA CTC TCA AAG AAT ACT TCA
--- --- --- --- --- --- --- --- --- --- --- --- --- --- --- --- --- ---
 N   S   T   Y   D   Y   F   L   L   P   A   G   L   S   K   N   T   S 279             288             297             306             315             324
AAT TCG AAT GGA CAT TAT GAG ACA GCT GTT GAA CCT AAG TTT AAT TCA AGT GGT
--- --- --- --- --- --- --- --- --- --- --- --- --- --- --- --- --- ---
 N   S   N   G   H   Y   E   T   A   V   E   P   K   F   N   S   S   G 333             342             351             360             369             378
ACT CAC TTT TCT AAC TTA TCC AAA GCA ACT TTC CAC TGT TGC TTT CGG AGT GAG
--- --- --- --- --- --- --- --- --- --- --- --- --- --- --- --- --- ---
 T   H   F   S   N   L   S   K   A   T   F   H   C   C   F   R   S   E 387             396             405             414             423             432
CAA GAT AGA AAC TGC TCC TTA TGT GCA GAC AAC ATT GAA GGA AGG ACA TTT GTT
--- --- --- --- --- --- --- --- --- --- --- --- --- --- --- --- --- ---
 Q   D   R   N   C   S   L   C   A   D   N   I   E   G   R   T   F   V
```

FIG.1A

```
      441         450         459         468         477         486
TCA ACA GTA AAT TCT TTA GTT TTT CAA CAA ATA GAT GCA AAC TGG AAC ATA CAG
--- --- --- --- --- --- --- --- --- --- --- --- --- --- --- --- --- ---
 S   T   V   N   S   L   V   F   Q   Q   I   D   A   N   W   N   I   Q 495         504         513         522         531         540
TGC TGG CTA AAA GGA GAC TTA AAA TTA TTC ATC TGT TAT GTG GAG TCA TTA TTT
--- --- --- --- --- --- --- --- --- --- --- --- --- --- --- --- --- ---
 C   W   L   K   G   D   L   K   L   F   I   C   Y   V   E   S   L   F 549         558         567         576         585         594
AAG AAT CTA TTC AGG AAT TAT AAC TAT AAG GTC CAT CTT TTA TAT GTT CTG CCT
--- --- --- --- --- --- --- --- --- --- --- --- --- --- --- --- --- ---
 K   N   L   F   R   N   Y   N   Y   K   V   H   L   L   Y   V   L   P 603         612         621         630         639         648
GAA GTG TTA GAA GAT TCA CCT CTG GTT CCC CAA AAA GGC AGT TTT CAG ATG GTT
--- --- --- --- --- --- --- --- --- --- --- --- --- --- --- --- --- ---
 E   V   L   E   D   S   P   L   V   P   Q   K   G   S   F   Q   M   V 657         666         675         684         693         702
CAC TGC AAT TGC AGT GTT CAT GAA TGT TGT GAA TGT CTT GTG CCT GTG CCA ACA
--- --- --- --- --- --- --- --- --- --- --- --- --- --- --- --- --- ---
 H   C   N   C   S   V   H   E   C   C   E   C   L   V   P   V   P   T 711         720         729         738         747         756
GCC AAA CTC AAC GAC ACT CTC CTT ATG TGT TTG AAA ATC ACA TCT GGT GGA GTA
--- --- --- --- --- --- --- --- --- --- --- --- --- --- --- --- --- ---
 A   K   L   N   D   T   L   L   M   C   L   K   I   T   S   G   G   V 765         774         783         792         801         810
ATT TTC CGG TCA CCT CTA ATG TCA GTT CAG CCC ATA AAT ATG GTG AAG CCT GAT
--- --- --- --- --- --- --- --- --- --- --- --- --- --- --- --- --- ---
 I   F   R   S   P   L   M   S   V   Q   P   I   N   M   V   K   P   D 819         828         837         846         855         864
CCA CCA TTA GGT TTG CAT ATG GAA ATC ACA GAT GAT GGT AAT TTA AAG ATT TCT
--- --- --- --- --- --- --- --- --- --- --- --- --- --- --- --- --- ---
 P   P   L   G   L   H   M   E   I   T   D   D   G   N   L   K   I   S
```

FIG.1B

```
       873           882           891           900           909           918
TGG TCC AGC CCA CCA TTG GTA CCA TTT CCA CTT CAA TAT CAA GTG AAA TAT TCA
--- --- --- --- --- --- --- --- --- --- --- --- --- --- --- --- --- ---
 W   S   S   P   P   L   V   P   F   P   L   Q   Y   Q   V   K   Y   S 927           936           945           954           963           972
GAG AAT TCT ACA ACA GTT ATC AGA GAA GCT GAC AAG ATT GTC TCA GCT ACA TCC
--- --- --- --- --- --- --- --- --- --- --- --- --- --- --- --- --- ---
 E   N   S   T   T   V   I   R   E   A   D   K   I   V   S   A   T   S 981           990           999          1008          1017          1026
CTG CTA GTA GAC AGT ATA CTT CCT GGG TCT TCG TAT GAG GTT CAG GTG AGG GGC
--- --- --- --- --- --- --- --- --- --- --- --- --- --- --- --- --- ---
 L   L   V   D   S   I   L   P   G   S   S   Y   E   V   Q   V   R   G 1035          1044          1053          1062          1071          1080
AAG AGA CTG GAT GGC CCA GGA ATC TGG AGT GAC TGG AGT ACT CCT CGT GTC TTT
--- --- --- --- --- --- --- --- --- --- --- --- --- --- --- --- --- ---
 K   R   L   D   G   P   G   I   W   S   D   W   S   T   P   R   V   F 1089          1098          1107          1116          1125          1134
ACC ACA CAA GAT GTC ATA TAC TTT CCA CCT AAA ATT CTG ACA AGT GTT GGG TCT
--- --- --- --- --- --- --- --- --- --- --- --- --- --- --- --- --- ---
 T   T   Q   D   V   I   Y   F   P   P   K   I   L   T   S   V   G   S 1143          1152          1161          1170          1179          1188
AAT GTT TCT TTT CAC TGC ATC TAT AAG AAG GAA AAC AAG ATT GTT CCC TCA AAA
--- --- --- --- --- --- --- --- --- --- --- --- --- --- --- --- --- ---
 N   V   S   F   H   C   I   Y   K   K   E   N   K   I   V   P   S   K 1197          1206          1215          1224          1233          1242
GAG ATT GTT TGG TGG ATG AAT TTA GCT GAG AAA ATT CCT CAA AGC CAG TAT GAT
--- --- --- --- --- --- --- --- --- --- --- --- --- --- --- --- --- ---
 E   I   V   W   W   M   N   L   A   E   K   I   P   Q   S   Q   Y   D 1251          1260          1269          1278          1287          1296
GTT GTG AGT GAT CAT GTT AGC AAA GTT ACT TTT TTC AAT CTG AAT GAA ACC AAA
--- --- --- --- --- --- --- --- --- --- --- --- --- --- --- --- --- ---
 V   V   S   D   H   V   S   K   V   T   F   F   N   L   N   E   T   K
```

FIG.1C

```
      1305          1314          1323          1332          1341          1350
CCT CGA GGA AAG TTT ACC TAT GAT GCA GTG TAC TGC TGC AAT GAA CAT GAA TGC
--- --- --- --- --- --- --- --- --- --- --- --- --- --- --- --- --- ---
 P   R   G   K   F   T   Y   D   A   V   Y   C   C   N   E   H   E   C 1359          1368          1377          1386          1395          1404
CAT CAT CGC TAT GCT GAA TTA TAT GTG ATT GAT GTC AAT ATC AAT ATC TCA TGT
--- --- --- --- --- --- --- --- --- --- --- --- --- --- --- --- --- ---
 H   H   R   Y   A   E   L   Y   V   I   D   V   N   I   N   I   S   C 1413          1422          1431          1440          1449          1458
GAA ACT GAT GGG TAC TTA ACT AAA ATG ACT TGC AGA TGG TCA ACC AGT ACA ATC
--- --- --- --- --- --- --- --- --- --- --- --- --- --- --- --- --- ---
 E   T   D   G   Y   L   T   K   M   T   C   R   W   S   T   S   T   I 1467          1476          1485          1494          1503          1512
CAG TCA CTT GCG GAA AGC ACT TTG CAA TTG AGG TAT CAT AGG AGC AGC CTT TAC
--- --- --- --- --- --- --- --- --- --- --- --- --- --- --- --- --- ---
 Q   S   L   A   E   S   T   L   Q   L   R   Y   H   R   S   S   L   Y 1521          1530          1539          1548          1157          1566
TGT TCT GAT ATT CCA TCT ATT CAT CCC ATA TCT GAG CCC AAA GAT TGC TAT TTG
--- --- --- --- --- --- --- --- --- --- --- --- --- --- --- --- --- ---
 C   S   D   I   P   S   I   H   P   I   S   E   P   K   D   C   Y   L 1575          1584          1593          1602          1611          1620
CAG AGT GAT GGT TTT TAT GAA TGC ATT TTC CAG CCA ATC TTC CTA TTA TCT GGC
--- --- --- --- --- --- --- --- --- --- --- --- --- --- --- --- --- ---
 Q   S   D   G   F   Y   E   C   I   F   Q   P   I   F   L   L   S   G 1629          1638          1647          1656          1665          1674
TAC ACA ATG TGG ATT AGG ATC AAT CAC TCT CTA GGT TCA CTT GAC TCT CCA CCA
--- --- --- --- --- --- --- --- --- --- --- --- --- --- --- --- --- ---
 Y   T   M   W   I   R   I   N   H   S   L   G   S   L   D   S   P   P 1683          1692          1701          1710          1719          1728
ACA TGT GTC CTT CCT GAT TCT GTG GTG AAG CCA CTG CCT CCA TCC AGT GTG AAA
--- --- --- --- --- --- --- --- --- --- --- --- --- --- --- --- --- ---
 T   C   V   L   P   D   S   V   V   K   P   L   P   P   S   S   V   K
```

FIG.1D

```
      1737        1746        1755        1764        1773        1782
GCA GAA ATT ACT ATA AAC ATT GGA TTA TTG AAA ATA TCT TGG GAA AAG CCA GTC
--- --- --- --- --- --- --- --- --- --- --- --- --- --- --- --- --- ---
 A   E   I   T   I   N   I   G   L   L   K   I   S   W   E   K   P   V 1791        1800        1809        1818        1827        1836
TTT CCA GAG AAT AAC CTT CAA TTC CAG ATT CGC TAT GGT TTA AGT GGA AAA GAA
--- --- --- --- --- --- --- --- --- --- --- --- --- --- --- --- --- ---
 F   P   E   N   N   L   Q   F   Q   I   R   Y   G   L   S   G   K   E 1845        1854        1863        1872        1881        1890
GTA CAA TGG AAG ATG TAT GAG GTT TAT GAT GCA AAA TCA AAA TCT GTC AGT CTC
--- --- --- --- --- --- --- --- --- --- --- --- --- --- --- --- --- ---
 V   Q   W   K   M   Y   E   V   Y   D   A   K   S   K   S   V   S   L 1899        1908        1917        1926        1935        1944
CCA GTT CCA GAC TTG TGT GCA GTC TAT GCT GTT CAG GTG CGC TGT AAG AGG CTA
--- --- --- --- --- --- --- --- --- --- --- --- --- --- --- --- --- ---
 P   V   P   D   L   C   A   V   Y   A   V   Q   V   R   C   K   R   L 1953        1962        1971        1980        1989        1998
GAT GGA CTG GGA TAT TGG AGT AAT TGG AGC AAT CCA GCC TAC ACA GTT GTC ATG
--- --- --- --- --- --- --- --- --- --- --- --- --- --- --- --- --- ---
 D   G   L   G   Y   W   S   N   W   S   N   P   A   Y   T   V   V   M 2007        2016        2025        2034        2043        2052
GAT ATA AAA GTT CCT ATG AGA GGA CCT GAA TTT TGG AGA ATA ATT AAT GGA GAT
--- --- --- --- --- --- --- --- --- --- --- --- --- --- --- --- --- ---
 D   I   K   V   P   M   R   G   P   E   F   W   R   I   I   N   G   D 2061        2070        2079        2088        2097        2106
ACT ATG AAA AAG GAG AAA AAT GTC ACT TTA CTT TGG AAG CCC CTG ATG AAA AAT
--- --- --- --- --- --- --- --- --- --- --- --- --- --- --- --- --- ---
 T   M   K   K   E   K   N   V   T   L   L   W   K   P   L   M   K   N 2115        2124        2133        2142        2151        2160
GAC TCA TTG TGC AGT GTT CAG AGA TAT GTG ATA AAC CAT CAT ACT TCC TGC AAT
--- --- --- --- --- --- --- --- --- --- --- --- --- --- --- --- --- ---
 D   S   L   C   S   V   Q   R   Y   V   I   N   H   H   T   S   C   N
```

FIG.1E

```
         2169            2178            2187            2196            2205            2214
GGA ACA TGG TCA GAA GAT GTG GGA AAT CAC ACG AAA TTC ACT TTC CTG TGG ACA
--- --- --- --- --- --- --- --- --- --- --- --- --- --- --- --- --- ---
 G   T   W   S   E   D   V   G   N   H   T   K   F   T   F   L   W   T 2223            2232            2241            2250            2259            2268
GAG CAA GCA CAT ACT GTT ACG GTT CTG GCC ATC AAT TCA ATT GGT GCT TCT GTT
--- --- --- --- --- --- --- --- --- --- --- --- --- --- --- --- --- ---
 E   Q   A   H   T   V   T   V   L   A   I   N   S   I   G   A   S   V 2277            2286            2295            2304            2313            2322
GCA AAT TTT AAT TTA ACC TTT TCA TGG CCT ATG AGC AAA GTA AAT ATC GTG CAG
--- --- --- --- --- --- --- --- --- --- --- --- --- --- --- --- --- ---
 A   N   F   N   L   T   F   S   W   P   M   S   K   V   N   I   V   Q 2331            2340            2349            2358            2367            2376
TCA CTC AGT GCT TAT CCT TTA AAC AGC AGT TGT GTG ATT GTT TCC TGG ATA CTA
--- --- --- --- --- --- --- --- --- --- --- --- --- --- --- --- --- ---
 S   L   S   A   Y   P   L   N   S   S   C   V   I   V   S   W   I   L 2385            2394            2403            2412            2421            2430
TCA CCC AGT GAT TAC AAG CTA ATG TAT TTT ATT ATT GAG TGG AAA AAT CTT AAT
--- --- --- --- --- --- --- --- --- --- --- --- --- --- --- --- --- ---
 S   P   S   D   Y   K   L   M   Y   F   I   I   E   W   K   N   L   N 2439            2448            2457            2466            2475            2484
GAA GAT GGT GAA ATA AAA TGG CTT AGA ATC TCT TCA TCT GTT AAG AAG TAT ATA
--- --- --- --- --- --- --- --- --- --- --- --- --- --- --- --- --- ---
 E   D   G   E   I   K   W   L   R   I   S   S   S   V   K   K   Y   Y 2493            2502            2511            2520            2529            2538
ATC CAT GAT CAT TTT ATC CCC ATT GAG AAG TAC CAG TTC AGT CTT TAC CCA ATA
--- --- --- --- --- --- --- --- --- --- --- --- --- --- --- --- --- ---
 I   H   D   H   F   I   P   I   E   K   Y   Q   F   S   L   Y   P   I 2547            2556            2565            2574            2583            2592
TTT ATG GAA GGA GTG GGA AAA CCA AAG ATA ATT AAT AGT TTC ACT CAA GAT GAT
--- --- --- --- --- --- --- --- --- --- --- --- --- --- --- --- --- ---
 F   M   E   G   V   G   K   P   K   I   I   N   S   F   T   Q   D   D
```

FIG.1F

```
       2601            2610            2619            2628            2637            2646
ATT GAA AAA CAC CAG AGT GAT GCA GGT TTA TAT GTA ATT GTG CCA GTA ATT ATT
--- --- --- --- --- --- --- --- --- --- --- --- --- --- --- --- --- ---
 I   E   K   H   Q   S   D   A   G   L   Y   V   I   V   P   V   I   I 2655            2664            2673            2682            2691            2700
TCC TCT TCC ATC TTA TTG CTT GGA ACA TTA TTA ATA TCA CAC CAA AGA ATG AAA
--- --- --- --- --- --- --- --- --- --- --- --- --- --- --- --- --- ---
 S   S   S   I   L   L   L   G   T   L   L   I   S   H   Q   R   M   K 2709            2718            2727            2736            2745            2754
AAG CTA TTT TGG GAA GAT GTT CCG AAC CCC AAG AAT TGT TCC TGG GCA CAA GGA
--- --- --- --- --- --- --- --- --- --- --- --- --- --- --- --- --- ---
 K   L   F   W   E   D   V   P   N   P   K   N   C   S   W   A   Q   G 2763            2772            2781            2790            2799            2808
CTT AAT TTT CAG AAG ATG CTT GAA GGC AGC ATG TTC GTT AAG AGT CAT CAC CAC
--- --- --- --- --- --- --- --- --- --- --- --- --- --- --- --- --- ---
 L   N   F   Q   K   M   L   E   G   S   M   F   V   K   S   H   H   H 2817            2826            2835            2844            2853            2862
TCC CTA ATC TCA AGT ACC CAG GGA CAC AAA CAC TGC GGA AGG CCA CAG GGT CCT
--- --- --- --- --- --- --- --- --- --- --- --- --- --- --- --- --- ---
 S   L   I   S   S   T   Q   G   H   K   H   C   G   R   P   Q   G   P 2871            2880            2889            2898            2907            2916
CTG CAT AGG AAA ACC AGA GAC CTT TGT TCA CTT GTT TAT CTG CTG ACC CTC CCT
--- --- --- --- --- --- --- --- --- --- --- --- --- --- --- --- --- ---
 L   H   R   K   T   R   D   L   C   S   L   V   Y   L   L   T   L   P 2925            2934            2943            2952            2961            2970
CCA CTA TTG TCC TAT GAC CCT GCC AAA TCC CCC TCT GTG AGA AAC ACC CAA GAA
--- --- --- --- --- --- --- --- --- --- --- --- --- --- --- --- --- ---
 P   L   L   S   Y   D   P   A   K   S   P   S   V   R   N   T   Q   E 2979            2988
TGA TCA ATA AAA AAA AAA AAA 3'
--- --- --- --- --- --- ---
 *   S   I   K   K   K   K
```

FIG.1G

DETECTION OF A LEPTIN RECEPTOR VARIANT

The present application is a continuation-in-part of co-pending U.S. patent application Ser. No. 08/355,888, filed Dec. 14, 1994, which is a continuation-in-part of co-pending U.S. patent application Ser. No. 08/306,231, filed Sep. 14, 1994, each of which is incorporated by reference herein in its entirety.

INTRODUCTION

The present invention relates to a variant form of the receptor for the obese gene product. In particular, the invention relates to methods of detecting this receptor variant in cells and tissues of obese individuals. In addition, it relates to methods of inhibiting or down-regulating expression of this variant in cells to augment their responsiveness to weight regulation by leptin as well as methods of using compounds to directly activate signal transduction pathways associated with this ligand-receptor system.

BACKGROUND OF THE INVENTION

Obesity is not only a nutritional disorder in Western societies, it is also a serious health concern because of its association with adult-onset diabetes, hypertension, and heart disease (Grundy, 1990, *Disease-a-Month* 36:645–696). While there was evidence to suggest that body weight was physiologically regulated, the molecular mechanism has remained elusive. However, animal studies have produced several mouse strains that contain single-gene mutations, resulting in an obese phenotype. One such recessive mutation is manifested in the ob/ob mice, and it is referred to as the obese (ob) mutation.

Zhang et al. (1994, *Nature* 372:425–432) describe the cloning and sequencing of the mouse ob gene and its human homolog. When an isolated gene fragment was used as a probe, it was shown to hybridize with RNA only in white adipose tissue by northern blot analysis, but no expression was detected in any other tissue. In addition, the coding sequence of the ob gene hybridized to all vertebrate genomic DNAs tested, indicating a high level of conservation of this molecule among vertebrates. The deduced amino acid sequences are 84% identical between human and mouse, and both molecules contain features of secreted proteins.

In an effort to understand the physiologic function of the ob gene, several independent research groups produced recombinant ob gene product in bacteria for in vivo testing (Pelleymounter et al., 1995, *Science* 269:540–543; Halaas et al., 1995, *Science* 269:543–546; Campfield et al., 1995, *Science* 269:546–549). When the Ob protein (also known as leptin) was injected into grossly obese mice, which possessed two mutant copies of the ob gene, the mice exhibited a reduced appetite and began to lose weight. In addition, these studies described a dual action of leptin in both reducing the animals' food intake and in increasing their energy expenditure. Similarly, when normal mice received leptin, they also ate less than the untreated controls. More importantly, Campfield et al. (1995, *Science* 269:546–549) injected leptin directly into lateral ventricle, and observed a reduction in the animals' food intake, suggesting that leptin acts on central neuronal networks to regulate feeding behavior and energy balance. Thus, this result provides evidence that the leptin receptor (also known as OB-R) is expressed by cells in the brain.

Recently, a leptin fusion protein was generated and used to screen for OB-R in a cDNA expression library prepared from mouse choroid plexus, a tissue that lines brain cavities termed ventricles (Tartalia, 1995, *Cell* 83:1263–1271). This approach led to the cloning of one form of the OB-R coding sequence, which reveals a single membrane-spanning receptor, sharing structural similarities with several Class I cytokine receptors, such as the gp130 signal-transducing component of the interleukin-6 receptor (Taga et al., 1989, *Cell* 58:573–581), the granulocyte-colony stimulating factor receptor (Fukunaga et al., 1990, *Cell* 61:341–350), and the leukemia inhibitory factor receptor (Gearing et al., 1991, *EMBO J.* 10:2839–2848). Northern blot analysis and reverse transcription-polymerase chain reaction (RT-PCR) demonstrate that OB-R mRNA is expressed in several tissues, including lung, kidney, total brain, choroid plexus and hypothalamus.

The reported mouse OB-R protein contains a relatively short intracellular cytoplasmic domain as compared with other Class I cytokine receptors. Subsequently, when cDNA encoding its human homolog was isolated from a human infant brain library, the predicted human protein sequence contains a much longer intracellular domain. In view of this finding, it was speculated that different forms of the receptor might exist (Barinaga, 1996, *Science* 271:29). However, prior to the present invention, there was no report on the identification of any variant forms of the OB-R in humans or how such molecules, if they exist, would relate to obesity.

Additionally, several studies have shown that ob gene expression is actually increased in obese humans (Considine et al., 1995, *J. Clin. Invest.* 95:2986–2988; Lonnquist et al., 1995, *Nature Med.* 1:950; Hamilton et al., 1995, *Nature Med.* 1:953). Moreover, the mutations in the mouse Ob gene were not detected in human mRNA. Therefore, taken collectively, these studies imply that decreased leptin levels are not the primary cause of obesity, and argue for the presence of a less responsive receptor in obese individuals. There remains a need to isolate such an OB-R variant for the design of therapeutics to augment weight regulation by leptin.

SUMMARY OF THE INVENTION

The present invention relates to a variant form of the human OB-R. In particular, it relates to the detection of this receptor variant in cells of obese individuals, and methods for treating obesity by targeting this variant.

The invention is based, in part, upon the Applicants' discovery of human cDNA clones encoding a variant form of the OB-R. This receptor differs structurally from a reported OB-R with only three amino acid substitutions in the extracellular domain, but extensive diversity is observed in their intracellular cytoplasmic domains at the 3' end. The cytoplasmic domain of the variant of the invention is both shorter and distinct in nucleotide sequence from the corresponding domain of the published form of OB-R. In addition, its cytoplasmic domain is highly homologous to a human retrotransposon sequence. Therefore, a wide variety of uses are encompassed by the present invention, including but not limited to, the detection of the receptor variant in cells of obese individuals, methods to inhibit and/or down-regulate the expression of this receptor variant, gene therapy to replace the receptor variant in homozygous individuals, and direct activation of downstream signal transduction pathways in cells expressing the receptor variant for weight regulation.

BRIEF DESCRIPTION OF THE DRAWINGS

FIGS. 1A–1G Nucleotide sequence (SEQ ID NO:1) and deduced amino acid sequence (SEQ ID NOS:2, 3 and 4) of the human OB-R variant. The amino acid sequence diverges from the human OB-R reported by Tartaglia et al. (1995, Cell 83:1263–1271) at nucleotide residue #349, #422, #764 and from residue #2770 and beyond.

DETAILED DESCRIPTION OF THE INVENTION

The OB-R Variant

The present invention relates to nucleic acid and amino acid sequences of an OB-R variant in the Class I cytokine receptor family. In a specific embodiment by way of example in Section 6, infra, this variant was cloned and characterized. Amino acid sequence comparison of this OB-R variant with a published human OB-R sequence (Tartaglia et al., 1995, Cell 83:1263–1271) reveals three amino acid differences in their extracellular domain and extensive diversity in their intracellular cytoplasmic domains. More specifically, FIGS. 1A–1G shows that in the variant, nucleotide residues #349–351 encode alanine, nucleotide residues #421–423 encode arginine and nucleotide residues #763–765 encode arginine. Additionally, the variant diverges both in length and sequence composition from the published human OB-R sequence from nucleotide residue #2770 and beyond. In this regard, the intracellular domain of the variant is highly homologous to a retrotransposon sequence (Ono et al., 1987, Nucl. Acid. Res. 15:8725–8737).

In order to clone additional variant forms of the molecule, labeled DNA probes made from nucleic acid fragments corresponding to any portion of the cDNA disclosed herein may be used to screen a cDNA library prepared from human fetal liver, human lung, human kidney, human choroid plexus and human hypothalamus. More specifically, oligonucleotides corresponding to either the 5' or 3' terminus of the cDNA sequence may be used to obtain longer nucleotide sequences. Briefly, the library may be plated out to yield a maximum of 30,000 pfu for each 150 mm plate. Approximately 40 plates may be screened. The plates are incubated at 37° C. until the plaques reach a diameter of 0.25 mm or are just beginning to make contact with one another (3–8 hours). Nylon filters are placed onto the soft top agarose and after 60 seconds, the filters are peeled off and floated on a DNA denaturing solution consisting of 0.4N sodium hydroxide. The filters are then immersed in neutralizing solution consisting of 1M Tris HCL, pH 7.5, before being allowed to air dry. The filters are prehybridized in casein hybridization buffer containing 10% dextran sulfate, 0.5M NaCl, 50 mM Tris HCL, pH 7.5, 0.1% sodium pyrosphosphate, 1% casein, 1% SDS, and denatured salmon sperm DNA at 0.5 mg/ml for 6 hours at 60° C. The radiolabelled probe is then denatured by heating to 95° C. for 2 minutes and then added to the prehybridization solution containing the filters. The filters are hybridized at 60° C. for 16 hours. The filters are then washed in 1X wash mix (10X wash mix contains 3M NaCl, 0.6M Tris base, and 0.02M EDTA) twice for 5 minutes each at room temperature, then in 1X wash mix containing 1% SDS at 60° C. for 30 minutes, and finally in 0.3X wash mix containing 0.1% SDS at 60° C. for 30 minutes. The filters are then air dried and exposed to x-ray film for autoradiography. After developing, the film is aligned with the filters to select a positive plaque. If a single, isolated positive plaque cannot be obtained, the agar plug containing the plaques will be removed and placed in lambda dilution buffer containing 0.1M NaCl, 0.01M magnesium sulfate, 0.035M Tris HCl, pH 7.5, 0.01% gelatin. The phage may then be replated and rescreened to obtain single, well isolated positive plaques. Positive plaques may be isolated and the cDNA clones sequenced using primers based on the known cDNA sequence. This step may be repeated until a full length cDNA is obtained.

One method for identifying all 3' isoforms is to PCR amplify the 3' ends of the variant cDNA from a variety of tissues including but not limiting to, choroid plexus, hypothalamus, fetal liver, bone marrow, ovary, or prostate. To obtain the 3' end of the cDNA, an oligo-dT primer is used to synthesize the cDNA first strand. OB-R specific primers from the conserved region of the gene (e.g. up stream of nucleotide 2770) and oligo-dT are then used to amplify the 3' end. The PCR fragments are cloned and sequenced by standard techniques. Once obtained, these sequences may be translated into amino acid sequence and examined for certain landmarks such as continuous open reading frame, regulatory regions that associate with tyrosine kinase activation, and finally overall structural similarity to known OB-R variants.

Expression of the OB-R Variant

In accordance with the invention, the OB-R variant polynucleotide sequence which encodes a protein, peptide fragments, fusion proteins or functional equivalents thereof, may be used to generate recombinant DNA molecules that direct the expression of the protein, peptide fragments, fusion proteins or a functional equivalent thereof, in appropriate host cells. Such polynucleotide sequences, as well as other polynucleotides which selectively hybridize to at least a part of such polynucleotides or their complements, may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the expression of the OB-R variant. Such DNA sequences include those which are capable of hybridizing to the OB-R variant sequence under stringent conditions, particularly at its 3' end. The phrase "stringent conditions" as used herein refers to those hybridizing conditions that (1) employ low ionic strength and high temperature for washing, for example, 0.015M NaCl/0.0015M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75M NaCl, 0.075M Sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the OB-R variant sequence, which result in a silent change thus producing a functionally equivalent protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The DNA sequence of the invention may be engineered in order to alter the OB-R variant coding sequence for a variety of ends, including but not limited to, alterations which modify processing and expression of the gene product. For example, mutations may be introduced using techniques which are well known in the art, e.g., site-directed mutagenesis, to insert new restriction sites, to alter glycosylation patterns, phosphorylation, etc. In addition, the intracellular domain may also be altered and replaced by a different domain, such as the OB-R intracellular domain by Tartaglia et al.

In another embodiment of the invention, the OB-R variant sequence may be ligated to a heterologous sequence to encode a fusion protein. For example, for screening of peptide libraries for inhibitors or stimulators of receptor activity, it may be useful to encode a chimeric protein expressing a heterologous epitope that is recognized by a commercially available antibody. A fusion protein may also be engineered to contain a cleavage site located between the OB-R variant sequence and the heterologous protein sequence, so that the variant may be cleaved away from the heterologous moiety.

In an alternate embodiment of the invention, the coding sequence of the OB-R variant could be synthesized in whole or in part, using chemical methods well known in the art. (See, for example, Caruthers et al., 1980, *Nuc. Acids Res. Symp. Ser.* 7:215–233; Crea and Horn, 180, *Nuc. Acids Res.* 9(10):2331; Matteucci and Caruthers, 1980, *Tetrahedron Letters* 21:719; and Chow and Kempe, 1981, *Nuc. Acids Res.* 9(12):2807–2817). Alternatively, the protein itself could be produced using chemical methods to synthesize OB-R variant amino acid sequence in whole or in part. For example, peptides can be synthesized by solid phase techniques, cleaved from the resin, and purified by preparative high performance liquid chromatography. (e.g., see Creighton, 1983, *Proteins Structures And Molecular Principles,* W. H. Freeman and Co., N.Y. pp. 50–60). The composition of the synthetic peptides may be confirmed by amino acid analysis or sequencing (e.g., the Edman degradation procedure; see Creighton, 1983, *Proteins, Structures and Molecular Principles,* W. H. Freeman and Co., N.Y., pp. 34–49).

In order to express the OB-R variant in host cells, the nucleotide sequence coding for the variant, or a functional equivalent, is inserted into an appropriate expression vector, i.e., a vector which contains the necessary elements for the transcription and translation of the inserted coding sequence. The expressed gene products as well as host cells or cell lines transfected or transformed with recombinant OB-R variant expression vectors can be used for a variety of purposes. For example, host cells expressing the OB-R variant may be used to verify the ability of this molecule to bind leptin in a binding assay with radiolabeled, enzyme-conjugated or fluorescent dye-conjugated leptin. At the same time, the ability of the molecule to transduce an activation signal in host cells upon binding to leptin may be tested by assaying proliferation or phosphorylation pattern of kinases in the cells. In addition, genetically-engineered host cells can be used to screen for and select agonist and antagonist compounds, including any inhibitors that would interfere with binding of leptin to the extracellular domain of the OB-R variant. In that connection, such host cells may be used to screen for and select small molecules that can supplement the incomplete signal transduced by the OB-R variant following leptin binding. Other uses, include, but are not limited to generating antibodies (i.e., monoclonal or polyclonal) that competitively inhibit activity of an OB-R variant, neutralize its activity, or even enhances it activity. Antibodies may be used in detecting and quantifying expression of OB-R levels in cells and tissues.

Uses of the OB-R Variant Polynucleotide

The OB-R variant polynucleotide may be used for diagnostic and/or therapeutic purposes. For diagnostic purposes, the OB-R variant polynucleotide may be used to detect gene expression or aberrant gene expression in obese individuals as well as in normal individuals to identify predisposition for obesity. Included in the scope of the invention are oligonucleotide sequences, that include antisense RNA and DNA molecules, ribozymes and triplex DNA, that function to inhibit translation of OB-R variant.

Diagnostic Uses of OB-R Variant Polynucleotide

The OB-R variant polynucleotide may have a number of uses for the diagnosis of the possible causes underlying obesity, resulting from expression of the receptor variant. For example, the OB-R variant cytoplasmic domain DNA sequence may be used in hybridization assays of biopsies or autopsies to diagnose OB-R variant expression; e.g., Southern or Northern analysis, including in situ hybridization assays as well as PCR. Such techniques are well known in the art, and are in fact the basis of many commercially available diagnostic kits. For PCR detection, primers may be designed from a conserved region of the coding sequence and within the 3' region of OB-R variant. The tissues suitable for such analysis include but are not limited to, hypothalamus, choroid plexus, adipose tissues, lung, prostate, ovary, small intestine, bone marrow and peripheral blood mononuclear cells.

Therapeutic Uses of the OB-R Variant Polynucleotide

The OB-R variant polynucleotide may be useful in the treatment of various abnormal obese conditions. By introducing gene sequences into cells, gene therapy can be used to treat conditions in which the cells do not respond to leptin normally due to expression of the OB-R variant. In some instances, the polynucleotide encoding a functional OB-R is intended to replace or act in the place of the functionally deficient OB-R variant gene. Alternatively, abnormal conditions characterized by expression of two copies of the OB-R variant can be treated using the gene therapy techniques described below.

Non-responsiveness to normal levels of leptin is an important cause of obesity. This may result from a functionally defective receptor that does not transduce competent signals upon ligand binding. Recombinant gene therapy vectors, such as viral vectors, may be engineered to express signalling competent forms of OB-R which may be used to augment the non-responsiveness of the naturally occurring OB-R variant. A signalling competent form may be, for example, a protein with the same extracellular domain and transmembrane region, but containing all or part of its normal signal transduction domain, such as that described by Tartaglia et al. (1995, *Cell* 83:1263–1271). Thus recombinant gene therapy vectors may be used therapeutically for treatment of obesity resulting from expression or activity of the OB-R variant. Accordingly, the invention provides a method of augmenting signal transduction by an endogenous OB-R variant in a cell comprising delivering a DNA molecule encoding a signalling competent form of the OB-R to the cell so that the signalling competent protein is produced in the cell and competes with the endogenous defective OB-R variant for access to molecules in the signalling pathway which does not activate or are not activated by the endogenous natural defective receptor. Additionally, since dimerization of a functional receptor with a defective variant may occur in cells of heterozygous individuals, small molecules may be used to inhibit such pairing, thereby increasing the number of functional dimeric receptors for proper signalling in response to leptin.

In contrast, overexpression of either leptin or a competent OB-R may result in a clinical anorexic-like syndrome due to a loss of appetite or hypermetabolic activity. In such cases, the OB-R variant of the invention may be introduced into cells with functional receptors to cause a decrease in the number of functional receptors or to compete with such receptors for leptin binding.

Expression vectors derived from viruses such as retroviruses, vaccinia virus, adeno-associated virus, herpes viruses, or bovine papilloma virus, may be used for delivery of recombinant functional OB-R into the targeted cell population. Methods which are well known to those skilled in the art can be used to construct recombinant viral vectors containing an OB-R polynucleotide sequence. See, for example, the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y. Alternatively, recombinant OB-R molecules can be reconstituted into liposomes for delivery to target cells.

Oligonucleotide sequences including anti-sense RNA and DNA molecules and ribozymes that function to inhibit the translation of the OB-R variant mRNA are within the scope of the invention. Anti-sense RNA and DNA molecules act to directly block the translation of mRNA by binding to targeted mRNA and preventing protein translation. In regard to antisense DNA, oligodeoxyribonucleotides derived from the OB-R variant nucleotide sequence at nucleotide #2771 and beyond, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of OB-R variant RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Oligodeoxyribonucleotides can form sequence-specific triple helices by hydrogen bonding to specific complementary sequences in duplexed DNA. Interest in triple helices has focused on the potential biological and therapeutic applications of these structures. Formation of specific triple helices may selectively inhibit the replication and/or gene expression of targeted genes by prohibiting the specific binding of functional trans-acting factors.

Oligonucleotides to be used in triplex helix formation should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Oligonucleotide sequences may be pyrimidine-based, which will result in TAT and CGC triplets across the three associated strands of the resulting triple helix. The pyrimidine-rich oligonucleotides provide base complementarity to a purine-rich region of a single strand of the duplex in a parallel orientation to that strand. In addition, oligonucleotides may be chosen that are purine-rich, for example, containing a stretch of G residues. These oligonucleotides will form a triple helix with a DNA duplex that is rich in GC pairs, in which the majority of the purine residues are located on a single strand of the targeted duplex, resulting in GGC triplets across the three strands in the triplex. Alternatively, the potential sequences that can be targeted for triple helix formation may be increased by creating a so called "switchback" oligonucleotide. Switchback oligonucleotides are synthesized in an alternating 5'-3', 3'-5' manner, such that they base pair with first one strand of a duplex and then the other, eliminating the necessity for a sizeable stretch of either purines or pyrimidines to be present on one strand of a duplex.

Both anti-sense RNA and DNA molecules and ribozymes of the invention may be prepared by any method known in the art for the synthesis of RNA molecules. These include techniques for chemically synthesizing oligodeoxyribonucleotides well known in the art such as solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

Activation of Tyrosine Kinase Pathways in Obesity

Many known class I cytokine receptors initiate cell signaling via Janus kinases (JAKs) (Ihle, 1995, *Nature* 377:591–594; Heldin, 1995, *Cell* 80:213–223; Kishimoto et al, 1994, *Cell* 76:253–62; Ziemiecki et al, 1994, *Trends Cell. Biol.* 4:207–212). JAK1–3 have been shown to bind to conserved sequences termed box1 and box2 (Fukunaga et al., 1991, *EMBO J.* 10:2855–65; Murakami, 1991, *Proc. Natl. Acad. Sci. USA* 88:11349–53). Ligand binding induces a homo- or hetero-dimerization of receptor chains which activates, by phosphorylation, the JAKs. The activated JAKs, in turn, phosphorylate members of the STAT family (Heldin, 1995, *Cell* 80:213–223; Kishimoto et al., *Blood* 86:1243–54; Darnell et al., 1994, *Science* 264:1415–21; Zhong et al, 1994, *Proc. Natl. Acad. Sci. USA* 91:4806–10; Hou et al., 1994, *Science* 265:1701–6). These phosphorylated STATs ultimately translocate to the nucleus, form transcription complexes, and regulate gene expression. Both box1 and box2 are required for complete signaling in certain systems. (Fukunaga et al., 1991, *EMBO J.* 10:2855–65; Murakami, 1991, Proc. Natl. Acad. Sci. USA 88:11349–53). The OB-R variant disclosed herein has a typical box1 (from nucleotide #2707–2730) that contains the critical xWxxx-PxP amino acid sequence, but it does not contain an obvious box2 nor further downstream sequences that are important for normal receptor activation. Therefore, it is possible to use compounds that activate JAKs to directly activate these pathways for weight regulation without triggering the OB-R.

EXAMPLE

Molecular Cloning of an OB-R Variant

A number of cDNA clones were isolated from a human fetal liver cDNA library (Clontech, Palo Alto, Calif.), and the DNA sequences of several of these clones were determined. These clones (designated as Hu-B1.219 #4, #33, #34, #1, #36, #55, #60) contained overlapping sequences, which were then compiled into a contiguous nucleotide sequence (FIG. 1A–1G). When the deduced amino acid sequence of one such sequence was compared with the sequence of a recently published human OB-R, they were shown to be nearly identical in the extracellular domains with the exception of three amino acids, whereas there existed extensive diversity in their intracellular cytoplasmic domains at the 3' end. The predicted protein sequence contains two FN III domains, each containing a "WS box", which are characteristic of genes of the Class I cytokine receptor family. Therefore, the cDNA disclosed herein encodes an OB-R variant.

When various human tissue RNA were probed with a fragment of this OB-R variant by Northern blot analysis, expression of this molecule was detected in heart, placenta, lung, liver, muscle, pancreas, prostate, ovary, small intestine and brain.

Based on the sequence presented in FIG. 1A–1G, the translation initiation site appears at position #97. The sequence encodes an open reading frame up to and including nucleotide #2970. It is believed that the sequence between nucleotides #2629 and #2682 encodes a transmembrane domain. The complete sequence encodes a protein of 958 amino acids.

The sequence of the OB-R variant is identical to the sequence of human OB-R reported by Tartaglia (1995, *Cell* 83:1263–1271) in the transmembrane region and a portion of the intracellular domain up to and including nucleotide #2769, then they diverge at nucleotide #2770 and beyond. In addition, the product of this cDNA is substantially shorter in its intracellular domain than the published human OB-R. These two forms of OB-R may derive from a common precursor mRNA by an alternative splicing mechanism. The sequence in this region is consistent with well known splice junctions. It is noteworthy that the DNA sequence of the OB-R variant from nucleotide #2768 to the end is 98% identical to a human retrotransposon sequence that is thought to be derived from a human endogenous retroviral DNA sequence (Singer, 1982, *Cell* 28:433; Weiner et al., 1986, *Ann. Rev. Biochem.* 55:631; Lower et al., 1993, *Proc. Natl. Acad. Sci. USA* 90:4480; Ono et al., 1987, *Nucl. Acid. Res.* 15:8725–8735).

Deposit of Microorganisms

The following organisms were deposited with the American Type Culture Collection (ATCC), 12301 Parklawn Drive, Rockville, Md. 20852.

| Strain Designation | Accession No. |
| --- | --- |
| HuB1.219, #1 | 75885 |
| HuB1.219, #4 | 75886 |
| HuB1.219, #33 | 75888 |
| HuB1.219, #34 | 75889 |
| HuB1.219, #36 | 75890 |
| HuB1.219, #55 | 75971 |
| HuB1.219, #60 | 75973 |

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for detecting a nucleic acid encoding a leptin receptor variant in a cell, comprising:
  (a) contacting a nucleic acid molecule derived from the cell with a polynucleotide selected from the group consisting of
    (i) nucleotides #2770 through #2991 of SEQ ID NO:1;
    (ii) the complement of the polynucleotide of (i);
    (iii) a portion of the polynucleotide of (i) that specifically hybridizes to a nucleic acid comprising the polynucleotide of (ii); and
    (iv) a portion of the polynucleotide of (ii) that specifically hybridizes to a nucleic acid comprising the polynucleotide of (i); and
  (b) detecting hybridization of the polynucleotide with the nucleic acid molecule.

2. The method of claim 1 in which the polynucleotide comprises a nucleotide sequence as shown in SEQ ID NO:1 between #2770 and #2970 or a portion thereof, or its complementary sequence or a portion thereof.

3. The method of claim 1 in which the nucleic acid molecule is ribonucleic acid.

4. The method of claim 3 in which the ribonucleic acid is first extracted from the cell.

5. The method of claim 1 in which the nucleic acid molecule is deoxyribonucleic acid.

6. The method of claim 5 in which the deoxyribonucleic acid is first extracted from the cell.

7. The method of claim 1 in which the hybridization is detected by an in situ hybridization method.

8. The method of claim 1 in which the hybridization is detected by Northern blot analysis method.

9. The method of claim 1 in which the polynucleotide of step (a) is used as a primer in an amplification reaction.

10. The method of claim 9 in which the amplification reaction is the polymerase chain reaction.

11. The method of claim 1 in which the cell is obtained from hypothalamus.

12. The method of claim 1 in which the cell is obtained from choroid plexus.

13. The method of claim 1 in which the cell is obtained from adipose tissue.

14. The method of claim 1 in which the cell is obtained from lung.

15. The method of claim 1 in which the cell is obtained from prostate.

16. The method of claim 1 in which the cell is obtained from ovary.

17. The method of claim 1 in which the cell is obtained from small intestine.

18. The method of claim 1 in which the cell is obtained from bone marrow.

19. The method of claim 1 in which the cell is obtained from peripheral blood.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 2991 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:

(A) NAME/KEY: CDS
(B) LOCATION: 1..2991

(xi) SEQUENCE DESCRIPTION: SEQ ID NO:1:

```
GCG  CGC  GCG  ACG  CAG  GTG  CCC  GAG  CCC  CGG  CCC  GCG  CCC  ATC  TCT  GCC    48
Ala  Arg  Ala  Thr  Gln  Val  Pro  Glu  Pro  Arg  Pro  Ala  Pro  Ile  Ser  Ala
 1                   5                        10                       15

TTC  GGT  CGA  GTT  GGA  CCC  CCG  GAT  CAA  GGT  GTA  CTT  CTC  TGA  AGT  AAG    96
Phe  Gly  Arg  Val  Gly  Pro  Pro  Asp  Gln  Gly  Val  Leu  Leu   *   Ser  Lys
               20                        25                        30

ATG  ATT  TGT  CAA  AAA  TTC  TGT  GTG  GTT  TTG  TTA  CAT  TGG  GAA  TTT  ATT   144
Met  Ile  Cys  Gln  Lys  Phe  Cys  Val  Val  Leu  Leu  His  Trp  Glu  Phe  Ile
          35                        40                        45

TAT  GTG  ATA  ACT  GCG  TTT  AAC  TTG  TCA  TAT  CCA  ATT  ACT  CCT  TGG  AGA   192
Tyr  Val  Ile  Thr  Ala  Phe  Asn  Leu  Ser  Tyr  Pro  Ile  Thr  Pro  Trp  Arg
     50                        55                        60

TTT  AAG  TTG  TCT  TGC  ATG  CCA  CCA  AAT  TCA  ACC  TAT  GAC  TAC  TTC  CTT   240
Phe  Lys  Leu  Ser  Cys  Met  Pro  Pro  Asn  Ser  Thr  Tyr  Asp  Tyr  Phe  Leu
 65                        70                        75                        80

TTG  CCT  GCT  GGA  CTC  TCA  AAG  AAT  ACT  TCA  AAT  TCG  AAT  GGA  CAT  TAT   288
Leu  Pro  Ala  Gly  Leu  Ser  Lys  Asn  Thr  Ser  Asn  Ser  Asn  Gly  His  Tyr
                         85                        90                        95

GAG  ACA  GCT  GTT  GAA  CCT  AAG  TTT  AAT  TCA  AGT  GGT  ACT  CAC  TTT  TCT   336
Glu  Thr  Ala  Val  Glu  Pro  Lys  Phe  Asn  Ser  Ser  Gly  Thr  His  Phe  Ser
                    100                       105                       110

AAC  TTA  TCC  AAA  GCA  ACT  TTC  CAC  TGT  TGC  TTT  CGG  AGT  GAG  CAA  GAT   384
Asn  Leu  Ser  Lys  Ala  Thr  Phe  His  Cys  Cys  Phe  Arg  Ser  Glu  Gln  Asp
               115                       120                       125

AGA  AAC  TGC  TCC  TTA  TGT  GCA  GAC  AAC  ATT  GAA  GGA  AGG  ACA  TTT  GTT   432
Arg  Asn  Cys  Ser  Leu  Cys  Ala  Asp  Asn  Ile  Glu  Gly  Arg  Thr  Phe  Val
     130                       135                       140

TCA  ACA  GTA  AAT  TCT  TTA  GTT  TTT  CAA  CAA  ATA  GAT  GCA  AAC  TGG  AAC   480
Ser  Thr  Val  Asn  Ser  Leu  Val  Phe  Gln  Gln  Ile  Asp  Ala  Asn  Trp  Asn
145                       150                       155                       160

ATA  CAG  TGC  TGG  CTA  AAA  GGA  GAC  TTA  AAA  TTA  TTC  ATC  TGT  TAT  GTG   528
Ile  Gln  Cys  Trp  Leu  Lys  Gly  Asp  Leu  Lys  Leu  Phe  Ile  Cys  Tyr  Val
                         165                       170                       175

GAG  TCA  TTA  TTT  AAG  AAT  CTA  TTC  AGG  AAT  TAT  AAC  TAT  AAG  GTC  CAT   576
Glu  Ser  Leu  Phe  Lys  Asn  Leu  Phe  Arg  Asn  Tyr  Asn  Tyr  Lys  Val  His
                    180                       185                       190

CTT  TTA  TAT  GTT  CTG  CCT  GAA  GTG  TTA  GAA  GAT  TCA  CCT  CTG  GTT  CCC   624
Leu  Leu  Tyr  Val  Leu  Pro  Glu  Val  Leu  Glu  Asp  Ser  Pro  Leu  Val  Pro
               195                       200                       205

CAA  AAA  GGC  AGT  TTT  CAG  ATG  GTT  CAC  TGC  AAT  TGC  AGT  GTT  CAT  GAA   672
Gln  Lys  Gly  Ser  Phe  Gln  Met  Val  His  Cys  Asn  Cys  Ser  Val  His  Glu
     210                       215                       220

TGT  TGT  GAA  TGT  CTT  GTG  CCT  GTG  CCA  ACA  GCC  AAA  CTC  AAC  GAC  ACT   720
Cys  Cys  Glu  Cys  Leu  Val  Pro  Val  Pro  Thr  Ala  Lys  Leu  Asn  Asp  Thr
225                       230                       235                       240

CTC  CTT  ATG  TGT  TTG  AAA  ATC  ACA  TCT  GGT  GGA  GTA  ATT  TTC  CGG  TCA   768
Leu  Leu  Met  Cys  Leu  Lys  Ile  Thr  Ser  Gly  Gly  Val  Ile  Phe  Arg  Ser
                         245                       250                       255

CCT  CTA  ATG  TCA  GTT  CAG  CCC  ATA  AAT  ATG  GTG  AAG  CCT  GAT  CCA  CCA   816
Pro  Leu  Met  Ser  Val  Gln  Pro  Ile  Asn  Met  Val  Lys  Pro  Asp  Pro  Pro
                    260                       265                       270

TTA  GGT  TTG  CAT  ATG  GAA  ATC  ACA  GAT  GAT  GGT  AAT  TTA  AAG  ATT  TCT   864
Leu  Gly  Leu  His  Met  Glu  Ile  Thr  Asp  Asp  Gly  Asn  Leu  Lys  Ile  Ser
               275                       280                       285

TGG  TCC  AGC  CCA  CCA  TTG  GTA  CCA  TTT  CCA  CTT  CAA  TAT  CAA  GTG  AAA   912
Trp  Ser  Ser  Pro  Pro  Leu  Val  Pro  Phe  Pro  Leu  Gln  Tyr  Gln  Val  Lys
     290                       295                       300
```

| | | | | | | | | | | | | | | | | |
|---|---|---|---|---|---|---|---|---|---|---|---|---|---|---|---|---|
| TAT | TCA | GAG | AAT | TCT | ACA | ACA | GTT | ATC | AGA | GAA | GCT | GAC | AAG | ATT | GTC | 960 |
| Tyr | Ser | Glu | Asn | Ser | Thr | Thr | Val | Ile | Arg | Glu | Ala | Asp | Lys | Ile | Val | |
| 305 | | | | | 310 | | | | | 315 | | | | | 320 | |
| TCA | GCT | ACA | TCC | CTG | CTA | GTA | GAC | AGT | ATA | CTT | CCT | GGG | TCT | TCG | TAT | 1008 |
| Ser | Ala | Thr | Ser | Leu | Leu | Val | Asp | Ser | Ile | Leu | Pro | Gly | Ser | Ser | Tyr | |
| | | | | | 325 | | | | | 330 | | | | | 335 | |
| GAG | GTT | CAG | GTG | AGG | GGC | AAG | AGA | CTG | GAT | GGC | CCA | GGA | ATC | TGG | AGT | 1056 |
| Glu | Val | Gln | Val | Arg | Gly | Lys | Arg | Leu | Asp | Gly | Pro | Gly | Ile | Trp | Ser | |
| | | | | 340 | | | | | 345 | | | | | 350 | | |
| GAC | TGG | AGT | ACT | CCT | CGT | GTC | TTT | ACC | ACA | CAA | GAT | GTC | ATA | TAC | TTT | 1104 |
| Asp | Trp | Ser | Thr | Pro | Arg | Val | Phe | Thr | Thr | Gln | Asp | Val | Ile | Tyr | Phe | |
| | | | 355 | | | | | 360 | | | | | 365 | | | |
| CCA | CCT | AAA | ATT | CTG | ACA | AGT | GTT | GGG | TCT | AAT | GTT | TCT | TTT | CAC | TGC | 1152 |
| Pro | Pro | Lys | Ile | Leu | Thr | Ser | Val | Gly | Ser | Asn | Val | Ser | Phe | His | Cys | |
| | | 370 | | | | | 375 | | | | | 380 | | | | |
| ATC | TAT | AAG | AAG | GAA | AAC | AAG | ATT | GTT | CCC | TCA | AAA | GAG | ATT | GTT | TGG | 1200 |
| Ile | Tyr | Lys | Lys | Glu | Asn | Lys | Ile | Val | Pro | Ser | Lys | Glu | Ile | Val | Trp | |
| 385 | | | | | 390 | | | | | 395 | | | | | 400 | |
| TGG | ATG | AAT | TTA | GCT | GAG | AAA | ATT | CCT | CAA | AGC | CAG | TAT | GAT | GTT | GTG | 1248 |
| Trp | Met | Asn | Leu | Ala | Glu | Lys | Ile | Pro | Gln | Ser | Gln | Tyr | Asp | Val | Val | |
| | | | | 405 | | | | | 410 | | | | | 415 | | |
| AGT | GAT | CAT | GTT | AGC | AAA | GTT | ACT | TTT | TTC | AAT | CTG | AAT | GAA | ACC | AAA | 1296 |
| Ser | Asp | His | Val | Ser | Lys | Val | Thr | Phe | Phe | Asn | Leu | Asn | Glu | Thr | Lys | |
| | | | 420 | | | | | 425 | | | | | 430 | | | |
| CCT | CGA | GGA | AAG | TTT | ACC | TAT | GAT | GCA | GTG | TAC | TGC | TGC | AAT | GAA | CAT | 1344 |
| Pro | Arg | Gly | Lys | Phe | Thr | Tyr | Asp | Ala | Val | Tyr | Cys | Cys | Asn | Glu | His | |
| | | 435 | | | | | 440 | | | | | 445 | | | | |
| GAA | TGC | CAT | CAT | CGC | TAT | GCT | GAA | TTA | TAT | GTG | ATT | GAT | GTC | AAT | ATC | 1392 |
| Glu | Cys | His | His | Arg | Tyr | Ala | Glu | Leu | Tyr | Val | Ile | Asp | Val | Asn | Ile | |
| | 450 | | | | | 455 | | | | | 460 | | | | | |
| AAT | ATC | TCA | TGT | GAA | ACT | GAT | GGG | TAC | TTA | ACT | AAA | ATG | ACT | TGC | AGA | 1440 |
| Asn | Ile | Ser | Cys | Glu | Thr | Asp | Gly | Tyr | Leu | Thr | Lys | Met | Thr | Cys | Arg | |
| 465 | | | | | 470 | | | | | 475 | | | | | 480 | |
| TGG | TCA | ACC | AGT | ACA | ATC | CAG | TCA | CTT | GCG | GAA | AGC | ACT | TTG | CAA | TTG | 1488 |
| Trp | Ser | Thr | Ser | Thr | Ile | Gln | Ser | Leu | Ala | Glu | Ser | Thr | Leu | Gln | Leu | |
| | | | | 485 | | | | | 490 | | | | | 495 | | |
| AGG | TAT | CAT | AGG | AGC | AGC | CTT | TAC | TGT | TCT | GAT | ATT | CCA | TCT | ATT | CAT | 1536 |
| Arg | Tyr | His | Arg | Ser | Ser | Leu | Tyr | Cys | Ser | Asp | Ile | Pro | Ser | Ile | His | |
| | | | 500 | | | | | 505 | | | | | 510 | | | |
| CCC | ATA | TCT | GAG | CCC | AAA | GAT | GCT | TAT | TTG | CAG | AGT | GAT | GGT | TTT | TAT | 1584 |
| Pro | Ile | Ser | Glu | Pro | Lys | Asp | Cys | Tyr | Leu | Gln | Ser | Asp | Gly | Phe | Tyr | |
| | | 515 | | | | | 520 | | | | | 525 | | | | |
| GAA | TGC | ATT | TTC | CAG | CCA | ATC | TTC | CTA | TTA | TCT | GGC | TAC | ACA | ATG | TGG | 1632 |
| Glu | Cys | Ile | Phe | Gln | Pro | Ile | Phe | Leu | Leu | Ser | Gly | Tyr | Thr | Met | Trp | |
| | 530 | | | | | 535 | | | | | 540 | | | | | |
| ATT | AGG | ATC | AAT | CAC | TCT | CTA | GGT | TCA | CTT | GAC | TCT | CCA | CCA | ACA | TGT | 1680 |
| Ile | Arg | Ile | Asn | His | Ser | Leu | Gly | Ser | Leu | Asp | Ser | Pro | Pro | Thr | Cys | |
| 545 | | | | | 550 | | | | | 555 | | | | | 560 | |
| GTC | CTT | CCT | GAT | TCT | GTG | GTG | AAG | CCA | CTG | CCT | CCA | TCC | AGT | GTG | AAA | 1728 |
| Val | Leu | Pro | Asp | Ser | Val | Val | Lys | Pro | Leu | Pro | Pro | Ser | Ser | Val | Lys | |
| | | | | 565 | | | | | 570 | | | | | 575 | | |
| GCA | GAA | ATT | ACT | ATA | AAC | ATT | GGA | TTA | TTG | AAA | ATA | TCT | TGG | GAA | AAG | 1776 |
| Ala | Glu | Ile | Thr | Ile | Asn | Ile | Gly | Leu | Leu | Lys | Ile | Ser | Trp | Glu | Lys | |
| | | | 580 | | | | | 585 | | | | | 590 | | | |
| CCA | GTC | TTT | CCA | GAG | AAT | AAC | CTT | CAA | TTC | CAG | ATT | CGC | TAT | GGT | TTA | 1824 |
| Pro | Val | Phe | Pro | Glu | Asn | Asn | Leu | Gln | Phe | Gln | Ile | Arg | Tyr | Gly | Leu | |
| | | 595 | | | | | 600 | | | | | 605 | | | | |
| AGT | GGA | AAA | GAA | GTA | CAA | TGG | AAG | ATG | TAT | GAG | GTT | TAT | GAT | GCA | AAA | 1872 |
| Ser | Gly | Lys | Glu | Val | Gln | Trp | Lys | Met | Tyr | Glu | Val | Tyr | Asp | Ala | Lys | |
| | 610 | | | | | 615 | | | | | 620 | | | | | |

-continued

| | | | | | | | | | | | | | | | | |
|---|---|---|---|---|---|---|---|---|---|---|---|---|---|---|---|---|
| TCA | AAA | TCT | GTC | AGT | CTC | CCA | GTT | CCA | GAC | TTG | TGT | GCA | GTC | TAT | GCT | 1920 |
| Ser | Lys | Ser | Val | Ser | Leu | Pro | Val | Pro | Asp | Leu | Cys | Ala | Val | Tyr | Ala | |
| 625 | | | | 630 | | | | | 635 | | | | | 640 | | |
| GTT | CAG | GTG | CGC | TGT | AAG | AGG | CTA | GAT | GGA | CTG | GGA | TAT | TGG | AGT | AAT | 1968 |
| Val | Gln | Val | Arg | Cys | Lys | Arg | Leu | Asp | Gly | Leu | Gly | Tyr | Trp | Ser | Asn | |
| | | | | 645 | | | | | 650 | | | | | 655 | | |
| TGG | AGC | AAT | CCA | GCC | TAC | ACA | GTT | GTC | ATG | GAT | ATA | AAA | GTT | CCT | ATG | 2016 |
| Trp | Ser | Asn | Pro | Ala | Tyr | Thr | Val | Val | Met | Asp | Ile | Lys | Val | Pro | Met | |
| | | | 660 | | | | | 665 | | | | | 670 | | | |
| AGA | GGA | CCT | GAA | TTT | TGG | AGA | ATA | ATT | AAT | GGA | GAT | ACT | ATG | AAA | AAG | 2064 |
| Arg | Gly | Pro | Glu | Phe | Trp | Arg | Ile | Ile | Asn | Gly | Asp | Thr | Met | Lys | Lys | |
| | | 675 | | | | | 680 | | | | | 685 | | | | |
| GAG | AAA | AAT | GTC | ACT | TTA | CTT | TGG | AAG | CCC | CTG | ATG | AAA | AAT | GAC | TCA | 2112 |
| Glu | Lys | Asn | Val | Thr | Leu | Leu | Trp | Lys | Pro | Leu | Met | Lys | Asn | Asp | Ser | |
| | 690 | | | | | 695 | | | | | 700 | | | | | |
| TTG | TGC | AGT | GTT | CAG | AGA | TAT | GTG | ATA | AAC | CAT | CAT | ACT | TCC | TGC | AAT | 2160 |
| Leu | Cys | Ser | Val | Gln | Arg | Tyr | Val | Ile | Asn | His | His | Thr | Ser | Cys | Asn | |
| 705 | | | | | 710 | | | | | 715 | | | | | 720 | |
| GGA | ACA | TGG | TCA | GAA | GAT | GTG | GGA | AAT | CAC | ACG | AAA | TTC | ACT | TTC | CTG | 2208 |
| Gly | Thr | Trp | Ser | Glu | Asp | Val | Gly | Asn | His | Thr | Lys | Phe | Thr | Phe | Leu | |
| | | | | 725 | | | | | 730 | | | | | 735 | | |
| TGG | ACA | GAG | CAA | GCA | CAT | ACT | GTT | ACG | GTT | CTG | GCC | ATC | AAT | TCA | ATT | 2256 |
| Trp | Thr | Glu | Gln | Ala | His | Thr | Val | Thr | Val | Leu | Ala | Ile | Asn | Ser | Ile | |
| | | | 740 | | | | | 745 | | | | | 750 | | | |
| GGT | GCT | TCT | GTT | GCA | AAT | TTT | AAT | TTA | ACC | TTT | TCA | TGG | CCT | ATG | AGC | 2304 |
| Gly | Ala | Ser | Val | Ala | Asn | Phe | Asn | Leu | Thr | Phe | Ser | Trp | Pro | Met | Ser | |
| | | 755 | | | | | 760 | | | | | 765 | | | | |
| AAA | GTA | AAT | ATC | GTG | CAG | TCA | CTC | AGT | GCT | TAT | CCT | TTA | AAC | AGC | AGT | 2352 |
| Lys | Val | Asn | Ile | Val | Gln | Ser | Leu | Ser | Ala | Tyr | Pro | Leu | Asn | Ser | Ser | |
| | 770 | | | | | 775 | | | | | 780 | | | | | |
| TGT | GTG | ATT | GTT | TCC | TGG | ATA | CTA | TCA | CCC | AGT | GAT | TAC | AAG | CTA | ATG | 2400 |
| Cys | Val | Ile | Val | Ser | Trp | Ile | Leu | Ser | Pro | Ser | Asp | Tyr | Lys | Leu | Met | |
| 785 | | | | | 790 | | | | | 795 | | | | | 800 | |
| TAT | TTT | ATT | ATT | GAG | TGG | AAA | AAT | CTT | AAT | GAA | GAT | GGT | GAA | ATA | AAA | 2448 |
| Tyr | Phe | Ile | Ile | Glu | Trp | Lys | Asn | Leu | Asn | Glu | Asp | Gly | Glu | Ile | Lys | |
| | | | | 805 | | | | | 810 | | | | | 815 | | |
| TGG | CTT | AGA | ATC | TCT | TCA | TCT | GTT | AAG | AAG | TAT | TAT | ATC | CAT | GAT | CAT | 2496 |
| Trp | Leu | Arg | Ile | Ser | Ser | Ser | Val | Lys | Lys | Tyr | Tyr | Ile | His | Asp | His | |
| | | | 820 | | | | | 825 | | | | | 830 | | | |
| TTT | ATC | CCC | ATT | GAG | AAG | TAC | CAG | TTC | AGT | CTT | TAC | CCA | ATA | TTT | ATG | 2544 |
| Phe | Ile | Pro | Ile | Glu | Lys | Tyr | Gln | Phe | Ser | Leu | Tyr | Pro | Ile | Phe | Met | |
| | | 835 | | | | | 840 | | | | | 845 | | | | |
| GAA | GGA | GTG | GGA | AAA | CCA | AAG | ATA | ATT | AAT | AGT | TTC | ACT | CAA | GAT | GAT | 2592 |
| Glu | Gly | Val | Gly | Lys | Pro | Lys | Ile | Ile | Asn | Ser | Phe | Thr | Gln | Asp | Asp | |
| | 850 | | | | | 855 | | | | | 860 | | | | | |
| ATT | GAA | AAA | CAC | CAG | AGT | GAT | GCA | GGT | TTA | TAT | GTA | ATT | GTG | CCA | GTA | 2640 |
| Ile | Glu | Lys | His | Gln | Ser | Asp | Ala | Gly | Leu | Tyr | Val | Ile | Val | Pro | Val | |
| 865 | | | | 870 | | | | | 875 | | | | | 880 | | |
| ATT | ATT | TCC | TCT | TCC | ATC | TTA | TTG | CTT | GGA | ACA | TTA | TTA | ATA | TCA | CAC | 2688 |
| Ile | Ile | Ser | Ser | Ser | Ile | Leu | Leu | Leu | Gly | Thr | Leu | Leu | Ile | Ser | His | |
| | | | | 885 | | | | | 890 | | | | | 895 | | |
| CAA | AGA | ATG | AAA | AAG | CTA | TTT | TGG | GAA | GAT | GTT | CCG | AAC | CCC | AAG | AAT | 2736 |
| Gln | Arg | Met | Lys | Lys | Leu | Phe | Trp | Glu | Asp | Val | Pro | Asn | Pro | Lys | Asn | |
| | | | 900 | | | | | 905 | | | | | 910 | | | |
| TGT | TCC | TGG | GCA | CAA | GGA | CTT | AAT | TTT | CAG | AAG | ATG | CTT | GAA | GGC | AGC | 2784 |
| Cys | Ser | Trp | Ala | Gln | Gly | Leu | Asn | Phe | Gln | Lys | Met | Leu | Glu | Gly | Ser | |
| | | 915 | | | | | 920 | | | | | 925 | | | | |
| ATG | TTC | GTT | AAG | AGT | CAT | CAC | CAC | TCC | CTA | ATC | TCA | AGT | ACC | CAG | GGA | 2832 |
| Met | Phe | Val | Lys | Ser | His | His | His | Ser | Leu | Ile | Ser | Ser | Thr | Gln | Gly | |
| | 930 | | | | | 935 | | | | | 940 | | | | | |

```
CAC  AAA  CAC  TGC  GGA  AGG  CCA  CAG  GGT  CCT  CTG  CAT  AGG  AAA  ACC  AGA     2880
His  Lys  His  Cys  Gly  Arg  Pro  Gln  Gly  Pro  Leu  His  Arg  Lys  Thr  Arg
945            950                      955                      960

GAC  CTT  TGT  TCA  CTT  GTT  TAT  CTG  CTG  ACC  CTC  CCT  CCA  CTA  TTG  TCC     2928
Asp  Leu  Cys  Ser  Leu  Val  Tyr  Leu  Leu  Thr  Leu  Pro  Pro  Leu  Leu  Ser
                    965                      970                      975

TAT  GAC  CCT  GCC  AAA  TCC  CCC  TCT  GTG  AGA  AAC  ACC  CAA  GAA  TGA  TCA     2976
Tyr  Asp  Pro  Ala  Lys  Ser  Pro  Ser  Val  Arg  Asn  Thr  Gln  Glu   *   Ser
               980                      985                      990

ATA  AAA  AAA  AAA  AAA                                                              2991
Ile  Lys  Lys  Lys  Lys
               995
```

( 2 ) INFORMATION FOR SEQ ID NO:2:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Ala  Arg  Ala  Thr  Gln  Val  Pro  Glu  Pro  Arg  Pro  Ala  Pro  Ile  Ser  Ala
1                   5                        10                       15

Phe  Gly  Arg  Val  Gly  Pro  Pro  Asp  Gln  Gly  Val  Leu  Leu
               20                  25
```

( 2 ) INFORMATION FOR SEQ ID NO:3:

( i ) SEQUENCE CHARACTERISTICS:
        ( A ) LENGTH: 960 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Ser  Lys  Met  Ile  Cys  Gln  Lys  Phe  Cys  Val  Val  Leu  Leu  His  Trp  Glu
1                   5                        10                       15

Phe  Ile  Tyr  Val  Ile  Thr  Ala  Phe  Asn  Leu  Ser  Tyr  Pro  Ile  Thr  Pro
               20                  25                        30

Trp  Arg  Phe  Lys  Leu  Ser  Cys  Met  Pro  Pro  Asn  Ser  Thr  Tyr  Asp  Tyr
          35                       40                        45

Phe  Leu  Leu  Pro  Ala  Gly  Leu  Ser  Lys  Asn  Thr  Ser  Asn  Ser  Asn  Gly
     50                       55                  60

His  Tyr  Glu  Thr  Ala  Val  Glu  Pro  Lys  Phe  Asn  Ser  Ser  Gly  Thr  His
65                       70                       75                       80

Phe  Ser  Asn  Leu  Ser  Lys  Ala  Thr  Phe  His  Cys  Cys  Phe  Arg  Ser  Glu
               85                       90                       95

Gln  Asp  Arg  Asn  Cys  Ser  Leu  Cys  Ala  Asp  Asn  Ile  Glu  Gly  Arg  Thr
               100                      105                      110

Phe  Val  Ser  Thr  Val  Asn  Ser  Leu  Val  Phe  Gln  Gln  Ile  Asp  Ala  Asn
               115                      120                      125

Trp  Asn  Ile  Gln  Cys  Trp  Leu  Lys  Gly  Asp  Leu  Lys  Leu  Phe  Ile  Cys
          130                      135                      140

Tyr  Val  Glu  Ser  Leu  Phe  Lys  Asn  Leu  Phe  Arg  Asn  Tyr  Asn  Tyr  Lys
145                      150                      155                      160

Val  His  Leu  Leu  Tyr  Val  Leu  Pro  Glu  Val  Leu  Glu  Asp  Ser  Pro  Leu
```

165                           170                           175
Val  Pro  Gln  Lys  Gly  Ser  Phe  Gln  Met  Val  His  Cys  Asn  Cys  Ser  Val
               180                      185                      190

His  Glu  Cys  Cys  Glu  Cys  Leu  Val  Pro  Val  Pro  Thr  Ala  Lys  Leu  Asn
               195                      200                 205

Asp  Thr  Leu  Leu  Met  Cys  Leu  Lys  Ile  Thr  Ser  Gly  Gly  Val  Ile  Phe
     210                           215                      220

Arg  Ser  Pro  Leu  Met  Ser  Val  Gln  Pro  Ile  Asn  Met  Val  Lys  Pro  Asp
225                           230                      235                      240

Pro  Pro  Leu  Gly  Leu  His  Met  Glu  Ile  Thr  Asp  Asp  Gly  Asn  Leu  Lys
                    245                      250                      255

Ile  Ser  Trp  Ser  Ser  Pro  Pro  Leu  Val  Pro  Phe  Pro  Leu  Gln  Tyr  Gln
               260                      265                      270

Val  Lys  Tyr  Ser  Glu  Asn  Ser  Thr  Thr  Val  Ile  Arg  Glu  Ala  Asp  Lys
               275                      280                      285

Ile  Val  Ser  Ala  Thr  Ser  Leu  Leu  Val  Asp  Ser  Ile  Leu  Pro  Gly  Ser
     290                           295                      300

Ser  Tyr  Glu  Val  Gln  Val  Arg  Gly  Lys  Arg  Leu  Asp  Gly  Pro  Gly  Ile
305                      310                      315                           320

Trp  Ser  Asp  Trp  Ser  Thr  Pro  Arg  Val  Phe  Thr  Thr  Gln  Asp  Val  Ile
               325                      330                           335

Tyr  Phe  Pro  Pro  Lys  Ile  Leu  Thr  Ser  Val  Gly  Ser  Asn  Val  Ser  Phe
               340                      345                      350

His  Cys  Ile  Tyr  Lys  Lys  Glu  Asn  Lys  Ile  Val  Pro  Ser  Lys  Glu  Ile
          355                      360                      365

Val  Trp  Trp  Met  Asn  Leu  Ala  Glu  Lys  Ile  Pro  Gln  Ser  Gln  Tyr  Asp
     370                      375                      380

Val  Val  Ser  Asp  His  Val  Ser  Lys  Val  Thr  Phe  Phe  Asn  Leu  Asn  Glu
385                           390                      395                      400

Thr  Lys  Pro  Arg  Gly  Lys  Phe  Thr  Tyr  Asp  Ala  Val  Tyr  Cys  Cys  Asn
                    405                      410                      415

Glu  His  Glu  Cys  His  His  Arg  Tyr  Ala  Glu  Leu  Tyr  Val  Ile  Asp  Val
               420                      425                      430

Asn  Ile  Asn  Ile  Ser  Cys  Glu  Thr  Asp  Gly  Tyr  Leu  Thr  Lys  Met  Thr
          435                      440                      445

Cys  Arg  Trp  Ser  Thr  Ser  Thr  Ile  Gln  Ser  Leu  Ala  Glu  Ser  Thr  Leu
450                           455                      460

Gln  Leu  Arg  Tyr  His  Arg  Ser  Ser  Leu  Tyr  Cys  Ser  Asp  Ile  Pro  Ser
465                      470                      475                           480

Ile  His  Pro  Ile  Ser  Glu  Pro  Lys  Asp  Cys  Tyr  Leu  Gln  Ser  Asp  Gly
               485                      490                      495

Phe  Tyr  Glu  Cys  Ile  Phe  Gln  Pro  Ile  Phe  Leu  Leu  Ser  Gly  Tyr  Thr
               500                      505                      510

Met  Trp  Ile  Arg  Ile  Asn  His  Ser  Leu  Gly  Ser  Leu  Asp  Ser  Pro  Pro
          515                      520                      525

Thr  Cys  Val  Leu  Pro  Asp  Ser  Val  Val  Lys  Pro  Leu  Pro  Pro  Ser  Ser
     530                      535                      540

Val  Lys  Ala  Glu  Ile  Thr  Ile  Asn  Ile  Gly  Leu  Leu  Lys  Ile  Ser  Trp
545                      550                      555                           560

Glu  Lys  Pro  Val  Phe  Pro  Glu  Asn  Asn  Leu  Gln  Phe  Gln  Ile  Arg  Tyr
                    565                      570                      575

Gly  Leu  Ser  Gly  Lys  Glu  Val  Gln  Trp  Lys  Met  Tyr  Glu  Val  Tyr  Asp
               580                      585                      590

Ala Lys Ser Lys Ser Val Ser Leu Pro Val Pro Asp Leu Cys Ala Val
        595                 600                 605

Tyr Ala Tyr Gln Val Arg Cys Lys Arg Leu Asp Gly Leu Gly Tyr Trp
    610                 615                 620

Ser Asn Trp Ser Asn Pro Ala Tyr Thr Val Val Met Asp Ile Lys Val
625                 630                 635                 640

Pro Met Arg Gly Pro Glu Phe Trp Arg Ile Ile Asn Gly Asp Thr Met
            645                 650                 655

Lys Lys Glu Lys Asn Val Thr Leu Leu Trp Lys Pro Leu Met Lys Asn
                660                 665                 670

Asp Ser Leu Cys Ser Val Gln Arg Tyr Val Ile Asn His His Thr Ser
        675                 680                 685

Cys Asn Gly Thr Trp Ser Glu Asp Val Gly Asn His Thr Lys Phe Thr
    690                 695                 700

Phe Leu Trp Thr Glu Gln Ala His Thr Val Thr Val Leu Ala Ile Asn
705                 710                 715                 720

Ser Ile Gly Ala Ser Val Ala Asn Phe Asn Leu Thr Phe Ser Trp Pro
            725                 730                 735

Met Ser Lys Val Asn Ile Val Gln Ser Leu Ser Ala Tyr Pro Leu Asn
                740                 745                 750

Ser Ser Cys Val Ile Val Ser Trp Ile Leu Ser Pro Ser Asp Tyr Lys
        755                 760                 765

Leu Met Tyr Phe Ile Ile Glu Trp Lys Asn Leu Asn Glu Asp Gly Glu
    770                 775                 780

Ile Lys Trp Leu Arg Ile Ser Ser Ser Val Lys Lys Tyr Tyr Ile His
785                 790                 795                 800

Asp His Phe Ile Pro Ile Glu Lys Tyr Gln Phe Ser Leu Tyr Pro Ile
            805                 810                 815

Phe Met Glu Gly Val Gly Lys Pro Lys Ile Ile Asn Ser Phe Thr Gln
                820                 825                 830

Asp Asp Ile Glu Lys His Gln Ser Asp Ala Gly Leu Tyr Val Ile Val
        835                 840                 845

Pro Val Ile Ile Ser Ser Ser Ile Leu Leu Leu Gly Thr Leu Leu Ile
    850                 855                 860

Ser His Gln Arg Met Lys Lys Leu Phe Trp Glu Asp Val Pro Asn Pro
865                 870                 875                 880

Lys Asn Cys Ser Trp Ala Gln Gly Leu Asn Phe Gln Lys Met Leu Glu
            885                 890                 895

Gly Ser Met Phe Val Lys Ser His His His Ser Leu Ile Ser Ser Thr
                900                 905                 910

Gln Gly His Lys His Cys Gly Arg Pro Gln Gly Pro Leu His Arg Lys
        915                 920                 925

Thr Arg Asp Leu Cys Ser Leu Val Tyr Leu Leu Thr Leu Pro Pro Leu
    930                 935                 940

Leu Ser Tyr Asp Pro Ala Lys Ser Pro Ser Val Arg Asn Thr Gln Glu
945                 950                 955                 960

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

Ser Ile Lys Lys Lys Lys
1               5